(12) United States Patent
Zorich et al.

(10) Patent No.: US 6,534,666 B1
(45) Date of Patent: Mar. 18, 2003

(54) USE OF WATER AND ACIDIC WATER TO PURIFY LIQUID MOCVD PRECURSORS

(75) Inventors: Robert Sam Zorich, Carlsbad, CA (US); James Richard Thurmond, Temecula, CA (US); David Allen Roberts, Fogelsville, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 10/037,739

(22) Filed: Dec. 27, 2001

(51) Int. Cl.$^7$ ................ C07F 1/08; C07F 7/08
(52) U.S. Cl. ............ 556/41; 556/12; 556/40; 556/112; 556/117; 427/587
(58) Field of Search ............ 556/12, 40, 41, 556/112, 117; 427/587

(56) References Cited

U.S. PATENT DOCUMENTS

| | | | |
|---|---|---|---|
| 3,869,387 A | 3/1975 | Vargiu et al. ............. 210/54 |
| 4,064,220 A | 12/1977 | Alon ............. 423/321 |
| 4,124,504 A | 11/1978 | Munden ............. 210/50 |
| 4,442,303 A | 4/1984 | Mims ............. 560/191 |
| 4,594,131 A | 6/1986 | Maier ............. 203/24 |
| 5,085,731 A | 2/1992 | Norman et al. ............. 156/646 |
| 5,098,516 A | 3/1992 | Norman et al. ............. 156/666 |
| 5,158,686 A | 10/1992 | Kigel ............. 210/713 |
| 5,187,300 A | 2/1993 | Norman ............. 556/12 |
| 5,449,824 A | 9/1995 | Felman et al. ............. 562/580 |
| 5,663,391 A | * 9/1997 | Machida et al. ............. 556/12 |
| 5,681,446 A | 10/1997 | Betts ............. 205/503 |
| 5,767,301 A | * 6/1998 | Senzaki et al. ............. 556/9 |
| 6,096,913 A | 8/2000 | Norman et al. ............. 556/12 |
| 6,130,345 A | * 10/2000 | Doppelt ............. 556/12 |

\* cited by examiner

Primary Examiner—Porfirio Nazario-Gonzalez
(74) Attorney, Agent, or Firm—Geoffrey L. Chase

(57) ABSTRACT

This invention relates to an improvement in a purification process for producing those liquid copper based complexes of β-diketones and, particularly the monovalent copper complexes of β-diketones, which are suited for application by chemical vapor deposition in the electronics industry. In the basic process for preparing a copper based complex, a reactive copper compound is reacted with a fluorinated β-diketonate and an organo source such as an olefinic source or one having acetylenic unsaturation. Purification is effected by contacting reaction product with a double deionized deoxygenated water source and preferably an acid/water source. An aqueous layer and an organic layer are formed with the aqueous layer containing byproducts and the organic phase containing product.

30 Claims, No Drawings

USE OF WATER AND ACIDIC WATER TO PURIFY LIQUID MOCVD PRECURSORS

BACKGROUND OF THE INVENTION

In the electronics industry there is a steady trend towards manufacturing microprocessors of increasingly high speed and large information storage capacity. This requires the individual electrical devices such as transistors, etc. within the microprocessors to be fabricated at an increasingly small scale. The metallic electrical interconnects between the devices also need to be miniaturized. As device and interconnect dimensions fall below one-quarter of a micron, the choice of interconnect metal becomes critical.

A process for producing these microscopic metal features found in microprocessors and interconnects is CVD (Chemical Vapor Deposition). In this technique a volatile organometallic (OM) compound in the gas phase is contacted with areas of a circuit where growth of a metal film (i.e. interconnect) is required. A surface catalyzed chemical reaction then occurs which leads to deposition of the desired metal. Since this is a chemical reaction, there is a potential for it to provide surface selective metallization.

Chemical vapor deposition of copper metal using organometallic copper compounds has been widely used in the electronics industry for the above applications. One class of copper organometallics for this application is the copper+1 (β-diketonate)(L) complexes where (L) represents a suitable stabilizing ligand, typically a non-aromatic unsaturated group including silylolefins and silylalkynes. Typically, in the synthesis of copper+1 (β-diketonate)(L) complexes, the divalent by-product copper bis(β-diketonate) and unreacted β-diketone species can be encountered as impurities that need to be removed.

The following patents are representative of organometallic compounds for chemical vapor deposition in the electronics industry.

U.S. Pat. No. 5,085,731 discloses organometallic complexes base upon copper$^{+1}$(β-diketonate) (L) complexes where (L) is a silylolefin stabilizing ligand. These are represented by the formula:

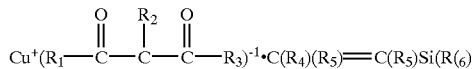

wherein $R_1$ and $R_3$ are each independently $C_1-C_8$ perfluoroalkyl, $R_2$ is H, F or $C_1-C_8$ perfluoroalkyl, $R_4$ is H, $C_1-C_8$ alkyl, or $Si(R_6)_3$, each $R_5$ is independently H or $C_1-C_8$ alkyl, and each $R_6$ is independently phenyl or $C_1-C_8$ alkyl. One type of complex is prepared by reacting a copper salt, e.g., copper chloride, the potassium salt of hexafluoroacetylacetone(i.e. K$^+$(hfac)), and a silylolefin in hexane or other solvent.

U.S. Pat. No. 5,187,300 discloses organometallic copper complexes suited for selectively depositing copper films onto electrically conducting portions under CVD conditions. The copper complexes are based upon copper(+1)(β-diketoneonate)(L) where (L) is a silylalkyne stabilizing ligand. One type of complex is prepared by the reaction of the potassium salt of hexafluoroacetylacetone with copper chloride in the presence of a silylalkyne stabilizing ligand.

These complexes have the formula:

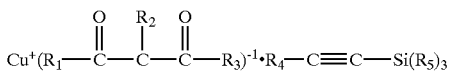

wherein $R_1$ and $R_3$ are each independently $C_1-C_8$ perfluoroalkyl, $R_2$ is H, F or $C_1-C_8$ perfluoroalkyl, $R_4$ is H, $C_1-C_8$ alkyl, phenyl, or $Si(R_5)_3$, and each $R_5$ is independently H or $C_1-C_8$ alkyl or phenyl.

U.S. Pat. No. 5,098,516 discloses organo copper based ligands of the formula:

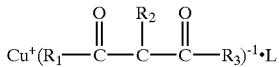

wherein $R_1$ and $R_3$ are each independently $C_1-C_8$ perfluoroalkyl, $R_2$ is H or $C_1-C_8$ perfluoroalkyl and L is carbon monoxide, an isonitrile or an unsaturated hydrocarbon ligand containing at least one non-aromatic unsaturation. These compounds are also prepared by the reaction of the potassium salt of hexafluoroacetylacetone with copper chloride in the presence of a stabilizing ligand.

U.S. Pat. No. 6,096,913 discloses the synthesis of copper (+1)(β-diketoneonate)(L) type complexes by the reaction of β-diketone with cuprous oxide in the presence of stabilizing ligand (L) and finely divided copper powder to suppress the formation of unwanted copper bis (hexafluoroacetylacetonate). The process is described by the following equation:

$$2Hfac + Cu_2O + 2(A) = 2copper + (hfac)(A) + H_2O$$

BRIEF SUMMARY OF THE INVENTION

This invention relates to a streamlined and cost effective process for the purification of Cu(+1)(β-diketonate) (L) liquid and solid complexes which are suitable for the chemical vapor deposition of copper. Solid Cu(+1)(β-diketonate) (L) complexes can be purified using this technique by first dissolving them in a suitable inert solvent then subjecting this solution to the treatment described below for liquid precursors.

In the basic process for preparing Cu(+1)(β-diketonate) (L) complexes, sometimes referred to as a monovalent copper β-diketone complex product, a reactive copper compound is treated with a coordinating anion such as the anion of hexafluoroacetylacetone or other coordinating anion such as a fluorinated β-ketoimine anion and, if required, a stabilizing ligand (L), typically bearing at least one unsaturation that is olefinic or acetylenic or is an amine or a phosphine. Depending upon the reactants employed, a monovalent copper based complex of a p-diketone represented by the formula below is generated:

Formula 1 where n is 1 and z is 1. Optionally, as shown, the complex is stabilized with a neutral ligand designated (L) as shown. L is selected from the group consisting of trimethylvinylsilane, alkenes, dienes, silicon substituted alkenes, silicon substituted dienes, alkynes, silicon substituted alkynes, alkyne-alkenes, silicon substituted alkynes-alkenes, nitriles, silicon substituted nitrites, isonitriles, silicon substituted isonitriles, carbon monoxide, trialkyl phosphines, triaryl phosphines, imines, diimines, amines and mixtures thereof.

Representative complexes are shown in formulas 2–4 when β-diketone coordinating anions are used:

Formula 2

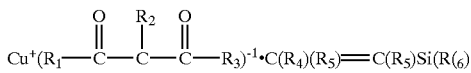

wherein $R_1$ and $R_3$ are each independently $C_1$–$C_8$ fluoroalkyl, $R_2$ is H, F or $C_1$–$C_8$ fluoroalkyl, $R_4$ is H, $C_1$–$C_8$ alkyl, or $Si(R_6)_3$, each $R_5$ is independently H or $C_1$–$C_8$ alkyl and each $R_6$ is independently phenyl or $C_1$–$C_8$ alkyl;

Formula 3

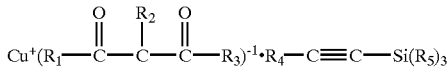

wherein $R_1$ and $R_3$ are each independently $C_1$–$C_8$ fluoroalkyl, $R_2$ is H, F or $C_1$–$C_8$ fluoroalkyl, $R_4$ is H, $C_1$–$C_8$ alkyl, or $Si(R_5)_3$, and each $R_5$ is independently H or $C_1$–$C_8$ alkyl or phenyl; and, Formula 4

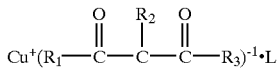

wherein $R_1$ and $R_3$ are each independently $C_1$–$C_8$ fluoroalkyl, $R_2$ is H or $C_1$–$C_8$ fluoroalkyl and L is carbon monoxide, an isonitrile or an unsaturated hydrocarbon ligand containing at least one non-aromatic unsaturation. Preferably, the fluoroalkyl groups in Formulas 2–4 are perfluoroalkyl.

In the syntheses of all of the above compounds it is typical for the crude reaction mixture to be contaminated with some divalent copper bis(β-diketonate) byproduct, sometimes referred to as divalent copper β-diketone complex byproduct, along with unreacted residual β-diketonate species either as free β-diketone or β-diketonate as a metal salt.

The improvement for removing unreacted fluorinated β-diketonate, e.g., Hhfac or the β-diketonate salt, e.g., Khfac from the reaction mixture comprises the following: contacting the reaction mixture with an effective amount of deionized water, preferably a degassed, and, most preferably, deoxygenated water, for solubilizing and extracting the unreacted fluorinated β-diketonate species into an aqueous phase. In the preferred case, which includes the removal of the divalent copper β-diketone complex by-product from the reaction mixture containing the monovalent copper(+1) (β-diketonate) (L) complex product, as well as other impurities, the process comprises: contacting the reaction product with a mixture of an acid and deoxygenated water under conditions for forming a water soluble divalent copper salt. The resulting aqueous phase is then separated thereby removing both the unreacted fluorinated β-diketonate species and the divalent copper bis(β-diketonate) by-product from the monovalent copper(+1) (β-diketonate) (L) complex product. Additionally, if cuprous oxide is used in the original syntheses and traces of it remain in the crude reaction mixture, then acid treatment also dissolve the oxide up into the aqueous phase as an additional purification benefit. Further, if excess stabilizing ligand (L) is present in the crude Cu(+1)(β-diketonate)(L) then it will also dissolve to a certain degree in the acid phase providing yet facilitating the purification step.

There are several advantages achieved by the practice of this process and these include:

an ability to simultaneously remove excess unreacted β-diketone species, byproduct divalent copper byproducts, e.g., $Cu(hfac)_2$ and copper oxide from the crude reaction product without significant yield loss;

an ability to reduce the level of excess silylolefin such as trimethylvinylsilane (TMVS) or other stabilizing ligand (L) compounds that are present in the copper complexes an ability to remove byproducts much faster than the conventional media absorbent processes; and, an ability to remove by products by means less costly than media absorbent processes.

DETAILED DESCRIPTION OF THE INVENTION

This invention relates to an improvement in a purification process for producing a monovalent copper(+1) (β-diketonate) (L) complex product and, particularly, a purification process for producing a monovalent copper complex of a β-diketone product which is suited for use in the microelectronics industry.

Representative reactive copper compounds from which to prepare a monovalent copper(+1) (β-diketonate) (L) complex product include cuprous oxide, cuprous chloride, cuprous bromide, cuprous acetate and other suitable copper (+1) compounds commonly used to prepare a monovalent copper(+1) (β-diketonate) (L) complex product.

Fluorinated β-diketones and fluorinated β-ketoimines from which monovalent copper(+1) (β-diketonate) (L) complex products can be prepared whose purification could be achieved by the process of this disclosure include: 1,1,1,5, 5,5-hexafluoro-2,4-pentanedione sometimes referred to herein as hexafluoroacetylacetone; 4-(2,2,2-trifluoroethyl) imino-1,1,1,5,5,5-hexafluoro-2-pentanone; 5-(2,2,2-trifluoroethyl)imino-1,1,1,2,2,6,6,6-octafluoro-3-hexanone, and 6-(2,2,2-trifluoroethyl)imino-1,1,1,2,2,3,3,7,7,7, -decafluoro4-heptanone.

The purification process is also suitable for purifying other copper (+1) compounds that are commingled with their analogous copper (+2) compounds (i.e., they share a common anion) or are contaminated with other copper (+2) species. Examples would be copper+1 β-diimines, β-ketoimines, acetates, amides, alkoxides, silanoates wherein the anions of these species are unfluorinated or fluorinated and wherein these compounds are either stabilized by coordination to a neutral ligand species such as an olefin, alkyne, amine or phosphine or they exist without such neutral ligand stabilization. An example of a neutral ligand stabilized species is copper(+1) trifluoroacetate(1,5-cyclooctadiene), an example of a copper(+1) compound not requiring a neutral stabilizing ligand is copper t-butoxide. Of the above copper compounds, those derived from fluorinated β-diketone, hexafluoroacetylacetone, is the one of particular interest and is generally used for purposes of description in these processes.

A wide variety of organo ligands (L) may be used as the stabilizing ligand for the organo portion of the copper complex when required and these include: isonitriles such as methylisocyanide and butyl isocyanide; olefins such as ethylene, hexadiene, dimethylbutene, dimethyl pentene, cyclooctene, 1,5-cyclooctadiene, cyclooctadecatriene and the like and acetylenics such as isopropylacetylene, diphenylacetylene. Silyolefins include trimethylvinylsilane TMVS) and trimethylsilyl propyne (TMSP).

In the basic process of preparing the monovalent copper complex of a β-diketone product, a reactive copper compound is reacted with the H-form or the K-form of a fluorinated β-diketone, e.g., the H-form or K form of hexafluoroacetylacetone (Hhfac) or (Kfac) respectively in the presence of an above described stabilizing ligand (L) and in the presence or absence of a solvent. As stated, supra, the unsaturation can be provided by a silylolefin or silyalkyne.

The improvement for removing the unreacted Hhfac or Khfac (or analogous acetic acid or acetate ion etc as listed above) from the reaction mixture comprises: contacting the reaction mixture with an effective amount of deoxygenated deionized water sufficient to form an aqueous phase to absorb the coordinating anion (X-) as either its metal salt or as its protonated form HX. Broadly from 10 to 1000 weight percent, typically, from 20 to 50 weight percent of water, based upon the weight of reaction mixture, is employed for the contacting step. Greater levels of water are not detrimental but serve no additional advantage. (Although some water may be created in the synthesis of the desired copper (+1) compound (as say in the reaction between Hhfac and cuprous oxide in the presence of (L) to from Cu(hfac)(L) plus water as described in U.S. Pat. No. 6,096,913) that amount of water is insufficient for effecting removal and separation.) Additionally, if sufficiently large quantities of HX are present to be removed, addition of water to effect its extraction into the aqueous phase may initially cause a majority of the HX to be precipitated out as a hydrate which can be conveniently filtered off prior to conducting the aqueous extraction process using a fresh charge of water. For instance, contacting fresh water with a batch of Cu(hfac)(L) containing a substantial level of free Hhfac will lead to much of the Hhfac precipitating out as solid Hhfac.dihydrate which can then be filtered off.

Removal of dissolved gases, and particularly dissolved oxygen, in the added water prior to the contacting step is desired for the success of the purification process. This avoids the potential for oxygen sensitive copper complexes to become oxidized in the purification process For Cu(hfac) (L) complexes it has been found that dissolved oxygen in the water can lead to the formation of copper oxide, thereby contaminating the product and thus potentially creating additional purification problems. As illustrated by this process, monovalent Cu(hfac)(L) based complexes are not adversely affected by water. Preferably deionized water is used which is passed through an ion exchange filter or media as is well known in the art. More preferably, the water is passed through the deionization process at least twice or through multiple deionization media or through a deionization process substantially equivalent to more than a single pass of the water through the treatment media sufficient to substantially reduce the undesired ion content of the water prior to treatment, i.e., for the purpose of the present invention, double deionized.

In the event that monovalent copper complex of a β-diketone free of a divalent copper complex of a β-diketone is desired, the undesired divalent copper complex of a β-diketone can be removed by washing with an acidic aqueous mixture. An acidic aqueous solution of from 0.1 to 2% acid may be used. Acids suited for use include, but are not limited to: nitric acid, sulfuric acid, hydrochloric acid, hydrofluoric acid, acetic acid. The key point in this is that the water content must exceed the free acid content by a large degree or the decomposition of the desired copper complex material may well occur. The level of acidic aqueous solution employed is the same as for the water wash alone.

In addition to removing contaminating copper(+2) species, such as the byproduct divalent copper complex of a β-diketone, the removal of unreacted β-diketone, β-ketoimine, β-diimine, acetate, etc. from the respective monovalent copper complex of a β-diketone is also a challenge. If the synthesis of the copper (+1) compound entails reacting the free ligand of the β-diketone, β-ketoimine etc with a reactive copper compound, as in say the synthesis of Cu(hfac) L complexes where the free ligand hexafluoroacetylacetone is reacted with cuprous oxide in the presence of (L), then any excess free ligand can be removed as described below. If the same monovalent copper complex of a β-diketone is made by reacting $K^+$hfac or similar metal 'salt' of Hhfac with cuprous chloride in the presence of (L), then unreacted $K^+$hfac can also be removed by the process. Typically, the prior art purification techniques for removing unwanted copper(+)2 species and unreacted 'hfac' etc have relied upon the use of adsorbent/chromatography techniques which are typically time consuming and costly.

Broadly, processing times may range from 0.2 to 2 hours depending upon the copper complex to be purified. Typical processing times is from 5–25 minutes. Good mixing and separation of the aqueous phase from the organic phase is key to short purification times. In contrast, a prior art chromatography separation operation can range from 4–8 kgs/hour for the same material. In addition, a chromatography process column may absorb up to 5 kgs of copper complex per 50 kilograms processed, so total yield loss can range to 10% in this one step.

Although not intending to be bound by theory, a typical mechanism that occurs in the purification process is that the deoxygenated water in excess will react with the unreacted H-form or K-form of the fluorinated β-diketonate, e.g., Hhfac, to form the water soluble hfac.dihydrate (HDH) per the following: Hfac+2 $H_2O \rightarrow$ Hfac.$2H_2O$. With respect to the divalent copper complex of a β-diketone, $Cu(hfac)_2$, that complex is converted to $Cu(NO_3)_2$ on reaction with nitric acid per the following equation: $Cu(hfac)_2 + 2HNO_3 \rightarrow Cu(NO_3)_2 + 2Hhfac$. Since $Cu(NO_3)_2$ is highly water soluble, it will dissolve preferentially into the water leaving no trace of $Cu(hfac)_2$ in the copper product. A similar reaction occurs when unreacted byproduct $Cu_2O$ is present in reaction mixture.

To summarize, an advantage of the water only addition to remove excess Hhfac or Khfac is that the reaction is self-limiting. Once the Hhfac or Khfac has reacted and formed Hhfac.dihydrate (HDH), all reactions cease, and there is no further action of the water on the finished product. An advantage of the acid/water washing vis-à-vis the water only washing step is that reaction of the acid with the copper (+2) species contaminated desired copper(+1) complex is a self-limiting reaction. When the reaction is complete, the acid is completely consumed, and will not allow further decomposition of the end product. By this reaction, then, the byproduct divalent copper complexes are converted to water soluble salts which dissolve in the water phase. These, water soluble salts are removed on separation of the aqueous phase from the organic phase.

Separation of the aqueous phase from the organic phase can be effected by conventional methods, e.g., decanting. Depending upon the hydrophobicity of the copper complex, separation may require the use of vacuum, inert gas sparging, a dehydrating media or combination for effecting complete separation of the two phases.

The following examples are intended to illustrate various embodiments of the invention.

General Procedure (a) Degassing and Oxygen Removal

Deionized water is degassed by placing an airtight vessel filled with water into an ultrasonic or megasonic bath at around room temperature. Elevated temperatures will speed the process of degassing up and may be used optionally. The "headspace" of the vessel is evacuated to a vacuum system and the vacuum pressure needs to be significantly below atmospheric pressure, approximately equal to or slightly above the vapor pressure of the water at process temperature. The water is observed visually until all signs of "boiling" have been eliminated. Up to one half of the water may be evaporated in the process, although the exact amount consumed is not relevant as long as all of the dissolved gas, particularly oxygen, is removed. It should be important to note that water may contain varying levels of dissolved oxygen and other gases and, as a result, degasification may take different amounts of time, and/or various vacuum pressures to completely remove. Degassing times may last for only a few minutes, or it may last for many hours.

(b) Byproduct Removal From Copper Complex

The raw (i.e., unwashed) monovalent β-diketone complex product contained in the reaction mixture is placed into a sealed flask in an inert atmosphere. It is important to confirm the vessel is clean of all debris and measures neutral (i.e., no acids, bases, or cleaning solvents are present) prior to adding the copper complex. A solution of water and 0.1% to 2% acid is mixed in with the raw copper material under an inert atmosphere and stirred vigorously. The solution should continue being stirred for 1–60 minutes, depending on the quantity and exact concentration of impurities. When completed, the resultant monovalent β-diketone complex product and water mixture will appear similar to an emulsion.

(c) Product Recovery

The monovalent β-diketone complex product is recovered by terminating stirring, and, then, allowing the monovalent β-diketone complex product and water to separate into an aqueous phase and an organic phase. Since the monovalent β-diketone complex product is almost completely hydrophobic, the water and divalent β-diketone complex byproduct separate cleanly and rapidly, with the lower density water floating to the top of the monovalent β-diketone complex product. Sometimes the water molecules may also adhere to the sidewalls of the vessel thus accelerating the separation of the water from monovalent β-diketone complex product.

The water then is removed from the top of the solution either through pouring, pipetting, decanting, or any other suitable means for separating bulk contents of one liquid from another. Following the gross removal of the water, the monovalent β-diketone complex product is transferred to a clean, dry vessel to eliminate any water-borne contamination from the water adhering to the side of the process flask or vessel. The spent water used in the purification process may range in color from clear to transparent blue, depending on the types and concentrations of impurities in the monovalent β-diketone complex product.

Residual water is removed from the monovalent β-diketone complex product by vacuum or by sparging with inert gas, or a combination of the two, to remove excess water. Given the low vapor pressure of most of the monovalent β-diketone complex products, the water is easily and rapidly removed, with a minimal amount of yield loss. Stripping of the residual water can also remove the silylolefin or silylalkyne or simply the olefin or alkyne depending upon the ligand used.

Following the stripping of excess water from the monovalent β-diketone complex products, additives as required for the process may be added to the material, and it can be packaged and shipped or prepared for subsequent processing.

COMPARATIVE EXAMPLE 1

Synthesis of $Cu^{+1}$(hfac).trimethylsilyl Propyne)

Under an atmosphere of nitrogen 0.178 moles of 1,1,1,5,5,5-hexafluoro-2,4-pentanedione (hfac) is slowly added over 30 minutes to 0.178 g of potassium hydride stirring in 150 ml of tetrahydrofuran (THF) at room temperature generating Khfac. Hydrogen gas is evolved and slight warming of the reaction occurred. The resultant solution is then transferred under nitrogen to another flask containing 0.178 moles of cuprous chloride and 0.178 g of trimethylsilyl propyne stirring in 150 ml of THF. The resultant mixture is then stirred at 60° C. for 2 hours during which time it is observed to turn a deep yellow color. Filtration under nitrogen followed by evaporation of THF from the filtrate yields a yellow crude reaction product. This is suspended in 100 ml of hexane, refiltered under nitrogen and the hexane evaporated to yield a yellow liquid.

COMPARATIVE EXAMPLE 2

Synthesis of $Cu^{+1}$(hfac).bis(trimethylsilyl)acetylene (i.e., $Cu^{+1}$ hfac)BTMSA The above synthesis shown in Comparative Example 1 is repeated, but substituting an equivalent quantity of bis(trimethylsilyl)acetylene for trimethylsilylpropyne. The final product is isolated as a yellow crystalline solid, mp 50° C.

EXAMPLE 3

Synthesis of $Cu^{+1}$(hfac).trimethylsilylpropyne With Water/Nitric Acid Purification The procedure of Example 1 is repeated except that a water/nitric acid wash is used to remove residual Khfac and byproduct $Cu^{++}$(hfac).trimethylsilylpropyne from $Cu^{+}$(hfac).trimethylsilylpropyne product in the reaction mixture This is accomplished by forming a 2% mixture of deoxygenated water per the general procedure and nitric acid. The acid/water mixture is stirred with the reaction mixture for about an hour. When stirring is terminated, an organic layer and a blue aqueous layer is formed indicating the presence of byproduct $Cu^{++}$(hfac).trimethylsilylpropyne. These layers are separated by decanting and the organic layer containing $Cu^{+}$(hfac).trimethylsilylpropyne product is dried and recovered.

EXAMPLE 4

Effect of Nitric Acid Concentration

The procedure of Example 1 is repeated except that trimethylvinylsilane is substituted for trimethylsilylpropyne in an appropriate amount and the H form of 1,1,1,5,5,5-hexafluoro-2,4-pentanedione (Hhfac) is used in place of the K form of 1,1,1,5,5,5-hexafluoro-2,4-pentanedione (Khfac). Three 500 mL samples of a reaction mixture containing $Cu^{+}$(hfac).TMVS product and byproducts Hfac and $Cu^{++}$(hfac)$_2$.TMVS are contacted with 75 mL of distilled water containing various levels of nitric acid. One sample is contacted with 75 mL of 0.5 wt % nitric acid, one with 75 mL of 0.2 wt % and one with 75 mL of water and no nitric acid.

Within five minutes the reaction mixtures contacted with the 0.5 and 0.2 nitric acid/water solutions turn to a yellow/clear solution. The water only solution requires about 45 to 50 minutes to allow for a change of color from a slightly green to a yellowish green.

The results show that an acid is required to remove the $Cu^{++}(hfac)_2 \cdot TMVS$ from the reaction mixture in efficient manner.

What is claimed is:

1. In a process for the removal of β-diketone byproducts from a reaction mixture containing a monovalent copper β-diketone complex product prepared by reacting a reactive copper compound with an H form or K form of a fluorinated β-diketone and, optionally, a stabilizing organic ligand (L), contaminated with the unreacted H form or K form fluorinated β-diketone and a divalent copper β-diketone complex byproduct, the improvement for removing the unreacted H form or K form fluorinated β-diketone from the reaction mixture which comprises:

contacting the reaction mixture with an effective amount of double deionized water for solubilizing the H form or K form fluorinated β-diketone;

forming an aqueous phase containing the H form or K form fluorinated β-diketone and an organic phase containing the monovalent copper β-diketone complex product;

separating the aqueous phase from the organic phase; and, recovering the monovalent copper β-diketone complex product.

2. The process of claim 1 wherein the water is degassed and deoxygenated.

3. The process of claim 2 wherein the water is added to the reaction mixture in an amount of from 10 to 1000 weight percent by weight of the reaction mixture.

4. The process of claim 3 wherein the monovalent copper β-diketone complex product is represented by the formula:

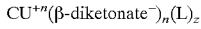

wherein β-diketone presents a fluorinated β-diketone anion, n is 1 and z is 1.

5. The process of claim 4 wherein L is the anion of the β-diketone selected from the group consisting of 1,1,1,5,5,5-hexafluoro-2,4-pentanedione; 4-(2,2,2-trifluoroethyl)imino-1, 1,1 ,5,5,5-hexafluoro-2-pentanone; 5-(2,2,2-trifluoroethyl)imino-1,1,1,2,2,6,6,6-octafluoro-3-hexanone, and 6-(2,2,2-trifluoroethyl)imino-1,1,1,2,2,3,3,7,7,7,-decafluoro-4-heptanone.

6. The process of claim 4 wherein the monovalent copper β-diketone complex product has a structural formula selected from the group consisting of:

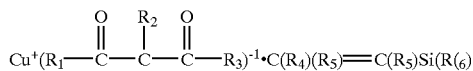

wherein $R_1$ and $R_3$ are each independently $C_1$–$C_8$ fluoroalkyl, $R_2$ is H, F or $C_1$–$C_8$ alkyl or fluoroalkyl, $R_4$ is H, $C_1$–$C_8$ alkyl, or $Si(R_6)_3$, each $R_5$ is independently H or $C_1$–$C_8$ alkyl and each $R_6$ is independently phenyl or $C_1$–$C_8$ alkyl; and,

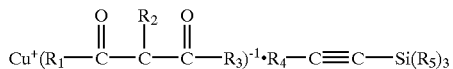

wherein $R_1$ and $R_3$ are each independently $C_1$–$C_8$ fluoroalkyl, $R_2$ is H, F or $C_1$–$C_8$ fluoroalkyl, $R_4$ is H, $C_1$–$C_8$ alkyl, or $Si(R_5)_3$, and each $R_5$ is independently H or $C_1$–$C_8$ alkyl or phenyl.

7. The process of claim 6 wherein the monovalent copper β-diketone complex product has the structural formula:

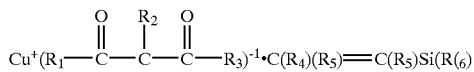

8. The process of claim 7 wherein $R_1$ and $R_3$ are trifluoromethyl.

9. The process of claim 8 wherein $R_2$ is H.

10. The process of claim 9 wherein each $R_5$ is H.

11. The process of claim 10 wherein $R_6$ is a methyl group.

12. The process of claim 11 wherein R4 is H.

13. The process of claim 4 wherein the fluorinated β-ketone is 1,1,1,5,5,5-hexafluoro-2,4-pentanedione and L is trimethylvinyl silane.

14. The process of claim 6 wherein the monovalent copper β-diketone complex product has the structural formula

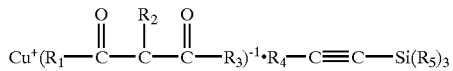

wherein $R_1$ and $R_3$ are each independently trifluoromethyl, $R_2$ is H, $R_4$ is H, and each $R_5$ is independently H.

15. In a process for the removal of β-diketone byproducts from a reaction mixture containing a monovalent copper β-diketone complex product prepared by reacting a reactive copper compound with an H form or K form fluorinated β-diketone and, optionally, a stabilizing organic ligand contaminated with unreacted H form or K form of a fluorinated β-diketone and a divalent copper β-diketone complex byproduct, the improvement for removing the unreacted H form or K form of the fluorinated β-diketone and the divalent copper β-diketone complex byproduct from the reaction mixture which comprises:

contacting the reaction mixture with an effective amount of a solution of acid and double deionized water for solubilizing the H form or K form fluorinated β-diketonate and divalent copper β-diketone complex byproduct;

forming an aqueous phase containing the H form or K form fluorinated β-diketone and divalent copper β-diketone complex byproduct and an organic phase containing the monovalent copper β-diketone complex product;

separating the aqueous phase from the organic phase; and, recovering the monovalent copper β-diketone complex product.

16. The process of claim 4 wherein the solution of acid and water contains from 0.1 to 2 percent by weight acid.

17. The process of claim 16 wherein the acid employed in forming the solution of acid and water is selected from the group consisting of nitric acid, sulfuric acid, hydrochloric acid, hydrofluoric acid, acetic acid, and mixtures thereof.

18. The process of claim 1 wherein the water is degassed and deoxygenated.

19. The process of claim 18 wherein the water is added to the reaction mixture in an amount of from 10 to 1000 weight percent by weight of the reaction mixture.

20. The process of claim 18 wherein the monovalent copper β-diketone complex product is represented by the formula:

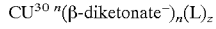

wherein β-diketone represents a fluorinated β-diketone anion, n is 1 and z is 1.

21. The process of claim 20 wherein L is the anion of the β-diketone selected from the group consisting of 1,1,1,5,5,5-hexafluoro-2,4-pentanedione; 4-(2,2,2-trifluoroethyl)imino-1, 1,1,5,5,5-hexafluoro-2-pentanone; 5-(2,2,2-trifluoroethyl)imino-1,1, 1,2,2,6,6,6-octafluoro-3-hexanone, and 6-(2,2,2-trifluoroethyl)imino-1,1,1,2,2,3,3,7,7,7,-decafluoro-4-heptanone.

22. The process of claim 20 wherein the monovalent copper β-diketone complex product has a structural formula selected from the group consisting of:

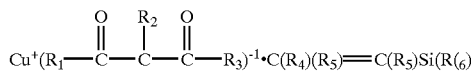

wherein $R_1$ and $R_3$ are each independently $C_1$–$C_8$ fluoroalkyl, $R_2$ is H, F or $C_1$–$C_8$ alkyl or fluoroalkyl, $R_4$ is H, $C_1$–$C_8$ alkyl, or $Si(R_6)_3$, each $R_5$ is independently H or $C_1$–$C_8$ alkyl and each $R_6$ is independently phenyl or $C_1$–$C_8$ alkyl; and,

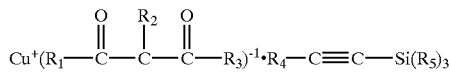

wherein $R_1$ and $R_3$ are each independently $C_1$–$C_8$ fluoroalkyl, $R_2$ is H, F or $C_1$–$C_8$ fluoroalkyl, $R_4$ is H, $C_1$–$C_8$ alkyl, or $Si(R_5)_3$, and each $R_5$ is independently H or $C_1$–$C_8$ alkyl or phenyl.

23. The process of claim 22 wherein the monovalent copper β-diketone complex product has the structural formula:

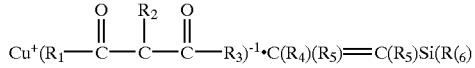

24. The process of claim 23 wherein $R_1$ and $R_3$ are trifluoromethyl.

25. The process of claim 24 wherein $R_2$ is H.

26. The process of claim 25 wherein each $R_5$ is H.

27. The process of claim 26 herein $R_6$ is a methyl group.

28. The process of claim 27 wherein $R_4$ is H.

29. The process of claim 20 wherein the fluorinated β-ketone is 1,1,1,5,5,5-hexafluoro-2,4-pentanedione and L is trimethylvinyl silane.

30. The process of claim 22 wherein the monovalent copper β-diketone complex product has the structural formula

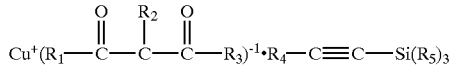

wherein $R_1$ and $R_3$ are each independently trifluoromethyl, $R_2$ is H, $R_4$ is H, and each $R_5$ is independently H.

* * * * *